(12) United States Patent
Preston et al.

(10) Patent No.: US 6,404,502 B2
(45) Date of Patent: *Jun. 11, 2002

(54) DUAL STANDARD GLOSS SENSOR

(75) Inventors: John G. Preston, Los Altos; Edward Belotserkovsky, San Francisco, both of CA (US)

(73) Assignee: Honeywell-Measurex Corporation, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/752,641

(22) Filed: Dec. 29, 2000

Related U.S. Application Data

(63) Continuation of application No. 09/123,502, filed on Jul. 28, 1998, now Pat. No. 6,233,053.
(60) Provisional application No. 60/054,063, filed on Jul. 29, 1997.

(51) Int. Cl.[7] ............................................... G01N 21/57
(52) U.S. Cl. ...................................................... 356/445
(58) Field of Search ................................ 356/445, 448, 356/447, 446, 429, 430

(56) References Cited

U.S. PATENT DOCUMENTS

| | | | | | |
|---|---|---|---|---|---|
| 3,636,361 | A | * | 1/1972 | Bowers | 356/448 |
| 3,780,299 | A | * | 12/1973 | Bock | 356/448 |
| 3,999,864 | A | * | 12/1976 | Mutter | 356/448 |
| 4,803,374 | A | * | 2/1989 | Monfort et al. | 356/446 |
| 5,106,196 | A | * | 4/1992 | Brierley | 356/445 |
| 5,401,977 | A | * | 3/1995 | Schwarz | 356/448 |
| 6,233,053 | B1 | * | 5/2001 | Preston et al. | 356/445 |

* cited by examiner

*Primary Examiner*—Richard A. Rosenberger
(74) *Attorney, Agent, or Firm*—Burns Doane; Anthony Miologos

(57) ABSTRACT

A single gloss sensor which can perform both DIN gloss measurement and DIN high gloss measurement, using the same hardware, and with minimal delay between the two measurements. The gloss sensor functions by directing light beams from a source to two different positions, either concurrently, or sequentially, between a position which measures gloss (75.degree) and a position which measures high gloss (45.degree). The gloss sensor also provides a reference light beam for correction of errors caused by the window glass, such as by dirt buildup.

6 Claims, 3 Drawing Sheets

DUAL STANDARD GLOSS SENSOR

This application is a continuation, of application Ser. No. 09/123,502, filed Jul. 28, 1998 now U.S. Pat. No. 6,233,053 which claims priority to Provisional Patent Application No. 60/054,063 filed Jul. 29, 1997 which are incorporated herein by reference in their entireties.

BACKGROUND OF THE INVENTION

The present invention relates generally to measurement of sheet surface characteristics, and more particularly to measurement of gloss and high gloss, on paper using a single device.

DESCRIPTION OF THE PRIOR ART

One of the parameters used in determining the quality of a surface is the surface luster or the gloss of the surface. For example, in paper production, various grades of paper having different surface gloss are produced to suit various applications. During paper production, it is desirable to periodically or continuously measure the gloss of the surface of the paper to ensure that the paper surface has the desired gloss.

Typically, the surface gloss of paper is measured using a gloss gauge during the last step of paper production before the finished paper, which is manufactured in a continuous sheet, is packaged in the form of rolls. The rolls of paper are then shipped to paper products manufacturers who process the paper sheet in accordance with the intended use.

Certain devices for determining the gloss of paper surfaces comprise an optical system which measures the intensity of a beam of light reflected from the paper surface. Typically, the gloss of the paper surface is determined by comparing its reflectance to the reflectance of a known gloss standard, such as, for example, a glass tile having a polished surface with a known gloss.

Specifically, in measuring the reflectance of the paper surface, light is projected onto the surface, and a sensor which is responsive to the intensity of light is positioned to measure the intensity of the light reflected from the paper surface. The gloss gauge measures the reflectance of a tile surface in the same manner by substituting the tile surface for the paper surface. The reflectance of the paper surface is referenced to the reflectance of the tile surface, thereby providing a measurement of the gloss of the paper surface. In practice, the reflectance measurement of the tile surface is periodically performed, off-sheet and between scans, as the gloss gauge scans back and forth across the paper surface. The gloss gauge is calibrated during each such measurement with the known reflectance of the tile surface.

Two gloss level measurements have evolved from this basic gloss gauging technique under DIN 54502. For regular gloss measurements, measurements are taken using a 75° angle for the incident light beam from perpendicular to the measured surface, and for high gloss, measurements are taken using a 45° angle for the incident light beam from perpendicular to the measured surface. Thus, if both measurements are desired on the same machine, in the past, two separate DIN standard measuring devices were needed. This double requirement not only causes a slower process, but also involves twice the equipment which must be purchased, maintained, and upgraded, etc. This situation is particularly troublesome considering the only difference between the two standards is the angle of the light beam striking the surface to be measured for gloss.

SUMMARY OF THE INVENTION

The present invention addresses the above issues by providing a single gloss sensor which can perform both the DIN gloss measurement and DIN high gloss measurement using the same hardware, and with minimal delay between the two measurements.

In a first embodyment, the invention functions by providing redirecting mirrors which alter the path of the light source used for the gloss measurements from a position which measures gloss (75°) to a position which measures high gloss (45°).

In a second embodiment, optical fibers direct measurement light beams to the necessary measurement angles.

DETAILED DESCRIPTION

Figure 1:
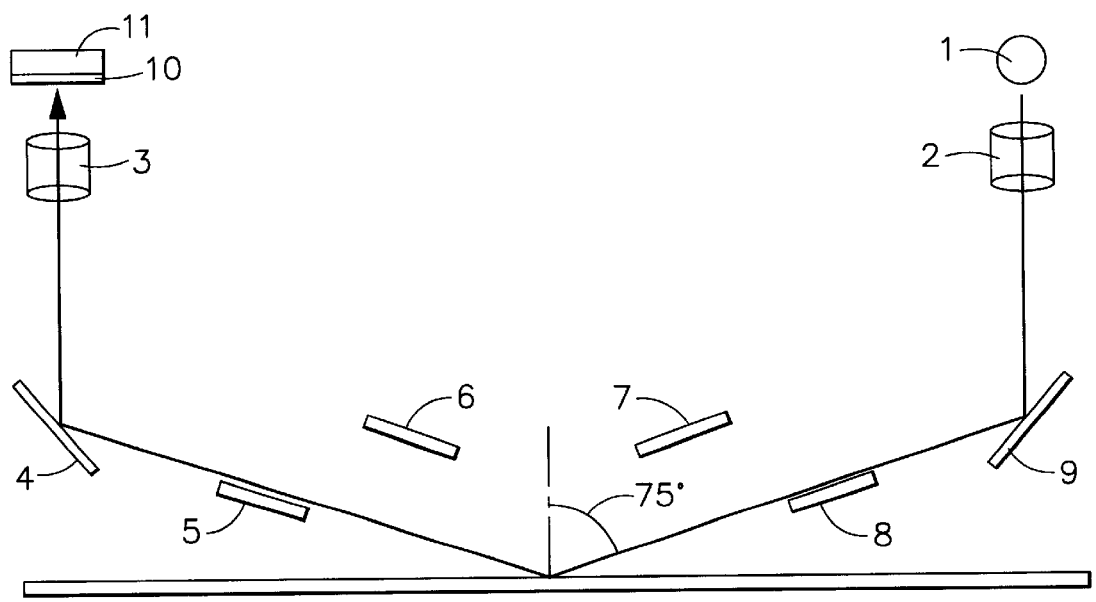
FIG. 1 shows a schematic diagram of a system incorporating the applicant's invention which is in position to take DIN gloss measurements.

A schematic diagram of a system incorporating the applicant's invention and which is in position to take DIN gloss measurements is shown in FIG. 1.

The disclosed gloss sensor consists of excitation source or lamp 1, first and second collimators 2 and 3, respectively, six mirrors 4–9 of which 5 and 8 are movable, filter 10, and detector 11, as shown in FIG. 1. Source or lamp 1 is a filament lamp which produces intense CW radiation in visible and IR regions.

To provide DIN gloss (75°) measurements. The radiation produced by source 1 is collimated by the first collimator 2 into a parallel beam, which is reflected by mirror 9 to the paper surface. As is shown in the FIG. 1, mirrors 5 and 8 are positioned out of the path of the beam from the laser source. In this mode, the parallel beams are incident on the paper plane with angle of 7520. The light beam reflected from the paper plane are thereafter directed by mirror 4 to second collimator 3, which condenses radiation on detector 11 after is passes through filter 10.

Figure 2:
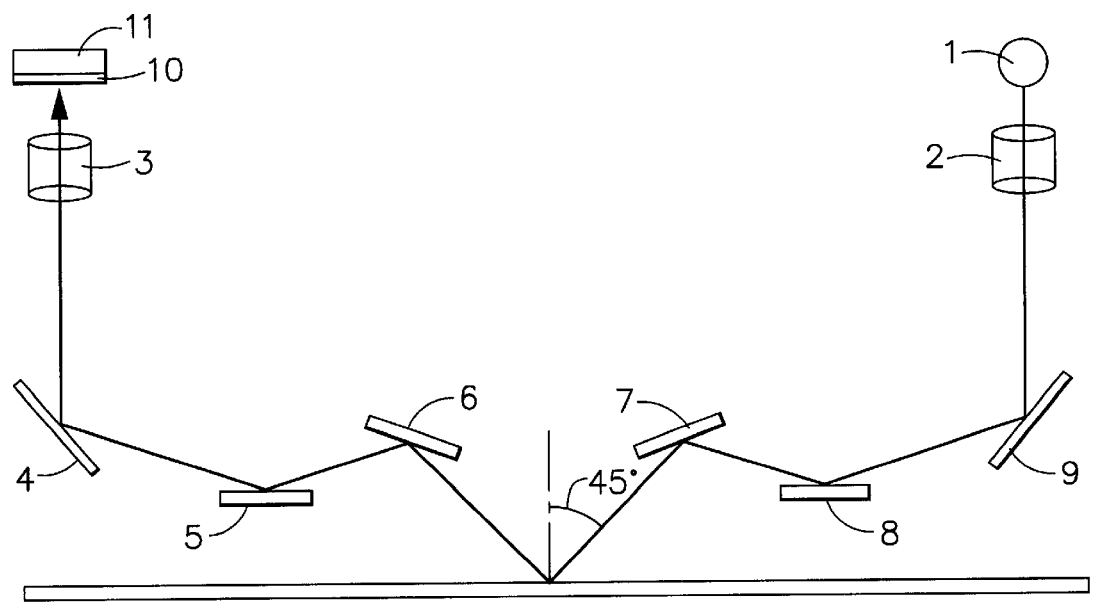
FIG. 2 shows a schematic diagram of a system incorporating the applicant's invention which is in position to take DIN high gloss measurements.

In order to provide DIN high gloss 45° measurements, mirrors 5 and 8 are rotated so that they cause the beam of light from light source 1 to reflect off mirrors 7 and 8 before striking the paper plane at an angle of 45°, as shown in FIG. 2. After specular reflection from the paper plane, the beam from source 1 reflects from mirror 6 to mirror 5. Finally, the beam reflects from mirror 4 through collimator 3 to detector 11, after passing through filter 10.

For both modes of operation, the coefficient of reflection from the paper surface is proportional to paper gloss. From the beam received at detector 11, the gloss may therefore be calculated.

Figure 3:
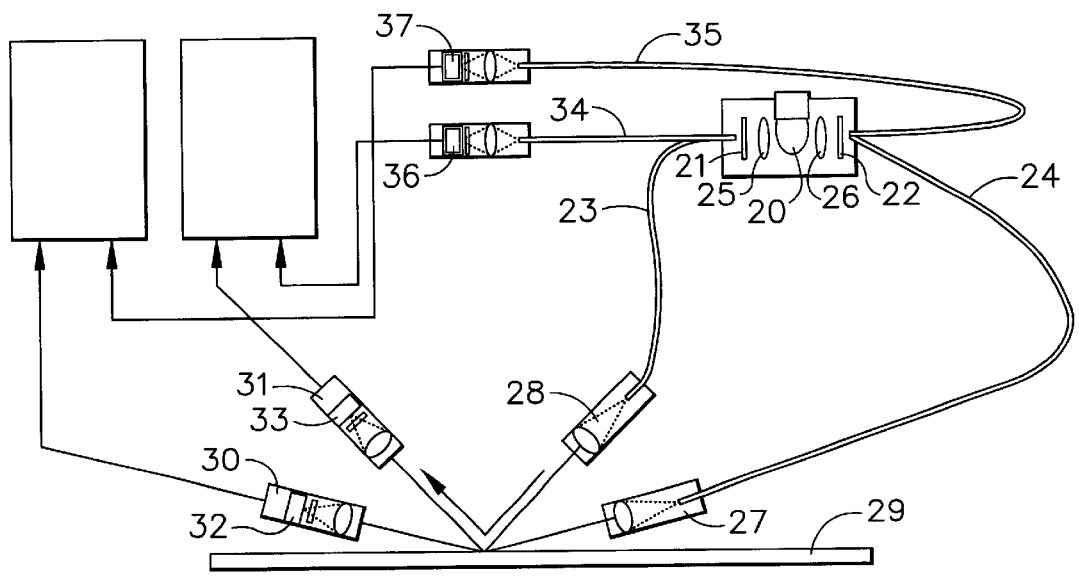
FIG. 3 shows the applicant's system implemented using optical fibers, rather than mirrors.

A second embodiment of the applicant's invention is shown in FIG. 3. In this system, optical fibers are used as the source of incident light beams. By using multiple optical fibers, measurement of both gloss and high gloss can be performed simultaneously. Like in the first embodiment, condencers and detectors are used on the receiving side of the sensor, to collect gloss signals.

A more detailed description of FIG. 3 is now provided. Source 20, is a filament lamp which produces intense CW radiation in visible and IR regions. The radiation is modulated by tuning forks 21 and 22, which for reasons to be described later, resonate at different frequencies. The radiation is focused on optical fibers 23 and 24, using lenses 25 and 26, respectively, which deliver radiation to collimators 28 and 27, respectively. The output tip of the optical fiber is practically an ideal point light source. The optical fibers serve as a diffuser and an optical mode mixer. The fiber tips are positioned at the focal point of the collimator lenses.

To correct for source variations or other system disturbances, further optical fibers 34 and 35 deliver optical radiation to reference detectors 36 and 37. The beams of radiation used for reference are split off after radiation from source 20 has passed through lenses 25 and 26, and tuning forks, 21 and 22 are used to modulate the signal. The reference is used to determine gloss by determining the percent of light reflection from the sample (i.e. paper 29) relative to the standard. The counts or units of the measurement channel are then divided by the counts on the reference channel to obtain a ratio. Gloss measurement is a slope times this ratio plus an offset.

In order to prevent interference between 45° and 75° channels, modulation of the light radiation is provided with different frequencies using the tuning forks 21 and 22.

Figure 4:
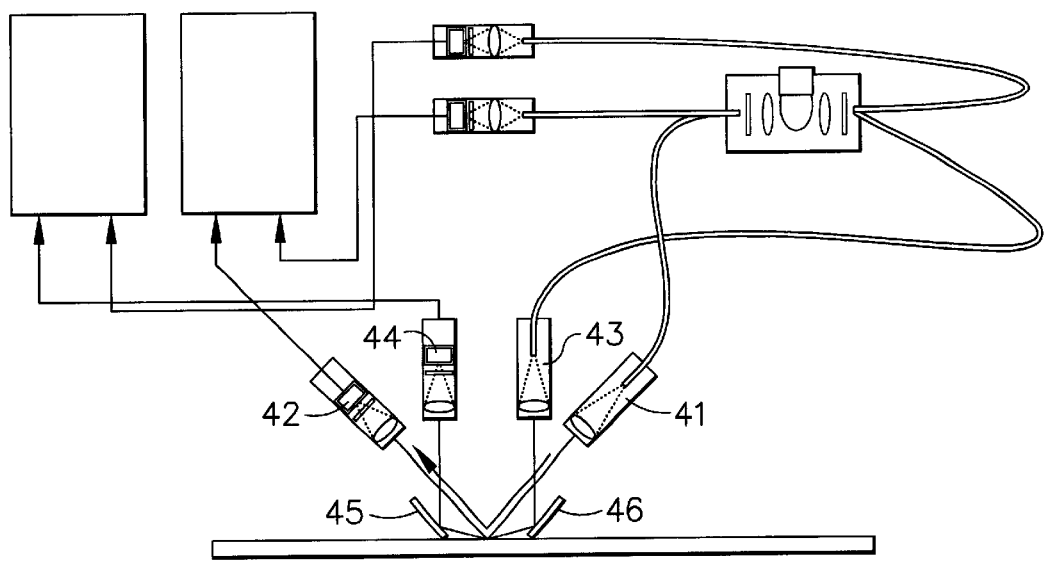
FIG. 4 shows a more compact system implemented using optical fibers.

A further modification of the embodiment is possible if conservation of space is a concern. FIG. 4 shows such a system. Collimator 41 and detector 42 for the 45° measurement are brought in closer to the measurement point, by moving 75° collimator 43 and detector 44 closer together, so that their incident and reflected beams are perpendicular to the measured surface. To provide the proper angle on the paper, additional lenses 45 and 46 are positioned to redirect incident and reflected beams to the necessary angles at the paper surface, and to detector 44, respectively.

Figure 5:
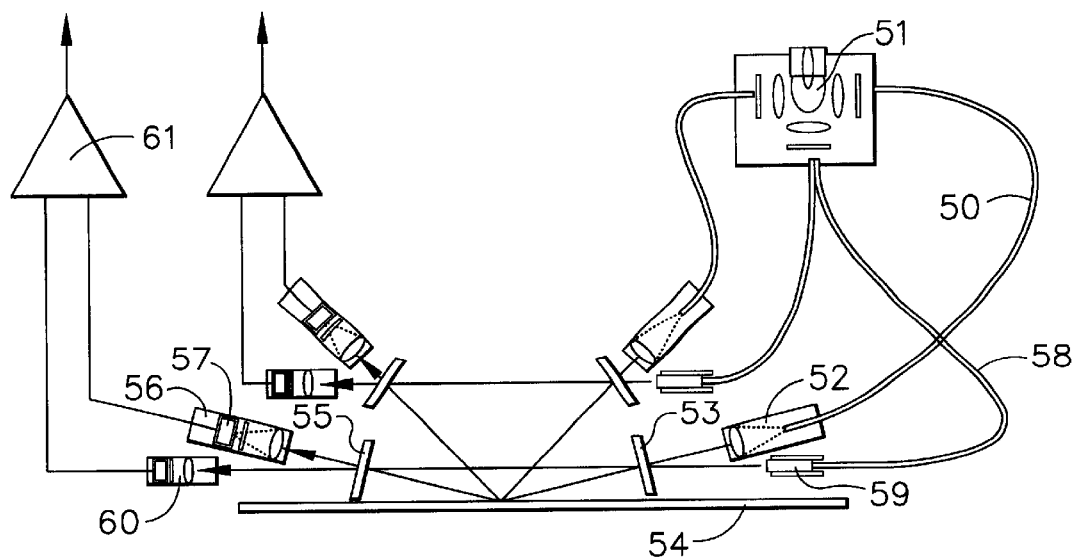
FIG. 5 shows a second scheme for first method gloss signal correction.
Figure 6:
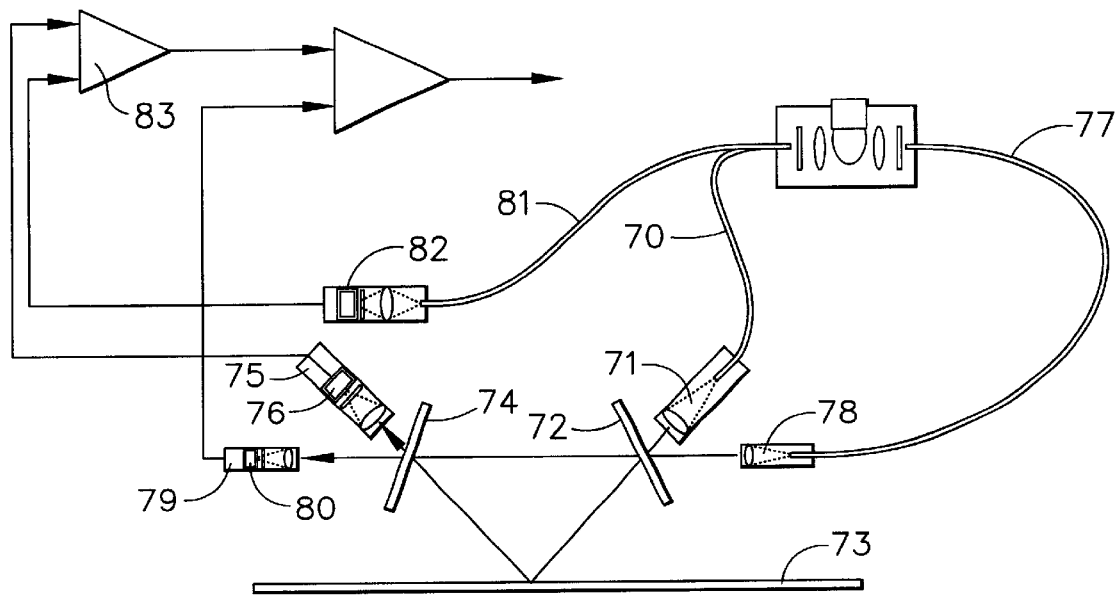
FIG. 6 shows a system including two step gloss signal correction.

Variations on the reference channel are also possible, as outlined in FIGS. 5 and 6, particularly for circumstances wherein the measurement beams must pass through sensor windows (i.e. glass) or some other optical disturbance likely to alter the measurement signal. For simplicity, the high gloss portions of the system have not been labeled in FIG. 5, since they are identical to the gloss components, only at a slightly different locations. In FIG. 5, optical fiber 50 delivers a light beam from source 51 in a similar manner to systems already described. After light from optical fiber 50 passes through collimator 52 the beam must pass through a glass window 53 to reach paper surface 54 to be measured. The reflected light beam must pass through another (or part of the same) glass window 55 before reaching a second collimator 56 and a detector 57. To compensate for dirt build-up on the glass windows, a reference fiber 58 passes a light beam through a GRIN (gradient index) lens 59, through the window glass 53, through second window 55, to reference beam detector 60. The reference beam must be modulated at a different frequency than either of the measured signals to prevent interference. Correction of errors caused by the window glass, such as dirt build-up are corrected by combining the measurement signal and the reference signal in a combining device 61.

As a further embodiment, both corrective signals could be used to improve the measurement accuracy since they each correct for a different error. A system using both reference measurements appears in FIG. 6. In this figure, the gloss (75°) measurement components have been omitted entirely for clarity. In the figure, an optic fiber 70 passes a measurement light beam to a collimator 71. The beam exits the collimator, passing through window 72, and thereafter strikes paper surface 73. The reflected light beam passes through window 74, which may or may not be the same glass as window 72. Collimator 75 receives this light beam and passes it to detector 76. To provide a first reference signal, a second optical fiber 77 passes a light beam through a GRIN lens 78, after being modulated to prevent interference with the measurement signal. The light beam, after exiting GRIN lens 78 passes through windows 72 and 74, striking reference collimator 79, and finally reference detector 80. At the same time, another optic fiber 81 passes a light bean to a reference/detector 82 directly. The measurement signal and the signal from reference/detector 82 are combined in a first combining device 83 to produce a first corrected signal. This corrected signal is thereafter combined with the references signal from detector 80 to form a final corrected gloss signal. From a practical standpoint, reference detector 82 corrects for source variations, while the signal from detector 80 corrects for window glass variations, such as paper dust build-up on the window glass.

Machine direction (MD) and cross direction (CD) DIN gloss and high gloss measurements may all be made with the same device by providing another set of sensors perpendicular to the shown set. In order to prevent interference between 45 and 75 degrees and MD and CD channels, modulation of the light radiation must be provided with different frequencies for each beam incident on the paper, for a total of four frequencies.

Thus since the invention disclosed herein may be embodied in other specific forms without departing from the spirit or general characteristics thereof, some of which forms have been indicated, the embodiments described herein are to be considered in all respects illustrative and not restrictive. For example, the disclosed sensor can provide also 20, 60, and 85 degrees specular gloss measurements according to ISO 2.813 standards. The scope of the invention is to be indicated by the appended claims, rather than by the foregoing description, and all changes which come within the meaning and range of equivalency of the claims are intended to be embraced therein.

We claim:

1. A dual standard gloss sensor for optically measuring the gloss of a sample surface comprising:
   a light beam source;
   first means for directing an incident light beam from the light beam source to the sample surface at a first angle;
   second means for directing an incident light beam from the light beam source to the sample surface at a second angle;
   first reflectance sensing means positioned to measure the intensity of the light beam reflected from the sample surface at said first angle;
   second reflectance sensing means positioned to measure the intensity of the light beam reflected from the sample surface at said second angle;
   means for directing one or more reference light beams, wherein the incident light beams and at least one reference light beam are directed at the same time; and
   at least a third reflectance sensing means positioned to measure the intensity of the one or more reference light beams, wherein at least one of the one or more reference light beams passes directly to the third reflectance sensing means to provide a reference of the light beam source's intensity.

2. The sensor of claim 1 wherein at least one reference light beam passes through similar optical disturbances as the beams incident on the paper to provide a reference of the intensity loss due to the optical disturbances.

3. The sensor of claim 1 in which the incident and reflected beams from said first and second means for direction an incident light beams lie parallel to the machine direction, further comprising:

third means for directing an incident light beam from the light beam source to the sample surface at a third angle;

fourth means for directing an incident light beam from the light beam source to the sample surface at a fourth angle;

third reflectance sensing means positioned to measure the intensity of the light beam reflected from the sample surface at said third angle; and fourth reflectance sensing means positioned to measure the intensity of the light beam reflected from the sample surface at said fourth angle;

wherein the incident and reflected beams from said third and fourth means for direction an incident light beams lie perpendicular to the machine direction.

4. The sensor of claim 1 wherein the first means for directing an incident light beam and the means for directing one or more reference light beams direct the incident light beam and the reference light beam through a same window at substantially a same location.

5. A dual standard gloss sensor for optically measuring the gloss of a sample surface comprising:

a first source of light;

a first mirror for causing an incident parallel beam of light from said source to strike the measuring surface at a first angle when in a first position, and to strike the measuring device at a second angle when in a second position; and a second mirror for receiving a parallel beam reflected from the sample surface at the first angle when in a first position, and for receiving a beam reflected from the sample surface at the second angle when in a second position.

6. The dual standard gloss sensor of claim 5 further comprising a third and fourth mirrors for directing the incident and reflected beams respectively, when said first and second mirrors are in at least their first or second positions.

* * * * *